United States Patent [19]

Gazzani

[11] Patent Number: 5,053,230

[45] Date of Patent: Oct. 1, 1991

[54] COSMETIC PREPARATIONS FOR PROMOTING TROPHISM OF THE SKIN AND OF RELATED HAIR FOLLICLES

[75] Inventor: Giovanni Gazzani, Appiano Gentile, Italy

[73] Assignee: Crinos Industria Farmacobiologica S.p.A., Como, Italy

[21] Appl. No.: 133,199

[22] Filed: Dec. 15, 1987

Related U.S. Application Data

[63] Continuation of Ser. No. 545,674, Oct. 25, 1983, abandoned.

[30] Foreign Application Priority Data

Oct. 29, 1982 [IT] Italy .............................. 23944 A/82
Jul. 13, 1983 [IT] Italy .............................. 22047 A/83

[51] Int. Cl.$^5$ ............................................. A61K 35/54
[52] U.S. Cl. ................................... 424/582; 424/520; 424/529; 424/70
[58] Field of Search ................................. 424/95, 582

[56] References Cited

FOREIGN PATENT DOCUMENTS 1098935 10/1968 United Kingdom .

OTHER PUBLICATIONS

KC Biological Inc. Catalogue-Products for Tissue Culture, pp. 28, 102, 103, 104 and 105.
Flow Laboratories Catalogue, pp. 24, 25, 72 and 74.
*Aliphatic Ammonium Salts in the Assay of Acidic Polysaccarides from Tissues*, Methods of Biochemical Analysis, vol. VIII, pp. 145-195.
Exhibit 1—*Dorland's Illustrated Medical Dictionary*, 24th Edition, pp. 886-887.
Exhibit 2—*Proceedings of the Society for Experimental Biology and Medicine*, vol. 73, No. 1, Jan. 1950, pp. 1-8.
Exhibit 3—*Cell and Tissue Culture*, John Paul, 2nd Edition, 1960, pp. 76-87.
Exhibit 4—Dorland's Illustrated Medical Dictionary, 24th Edition, pp. 1369-1371.

*Primary Examiner*—Sam Rosen
*Attorney, Agent, or Firm*—McAulay Fisher Nissen Goldberg & Kiel

[57] ABSTRACT

A cosmetic preparation is described as comprising at least an effective amount of a nutrient medium for the in vitro culture of isolated human epithelial cells and a related amount of serum of bovine fetus. The preparation is particularly active as a revitalizing agent for the skin, as an anti-wrinkle agent and as a factor for enhancing hair growth. The activity of the aforesaid nutrient medium can be furthermore enhanced by adding extractive mixtures, obtained from the connective tissues of animal organs, mainly mucopolysaccharides.

20 Claims, No Drawings

COSMETIC PREPARATIONS FOR PROMOTING TROPHISM OF THE SKIN AND OF RELATED HAIR FOLLICLES

This is a continuation of application Ser. No. 545,674, filed Oct. 25, 1983, now abandoned.

BACKGROUND OF THE INVENTION

The present invention relates to a cosmetic preparation for promoting trophism of the cutis and of the hair follicles. More particularly the present invention relates to a cosmetic preparation to be used as a revitalizing agent for the skin and as active factor for enhancing hair growth.

When the skin is pale, wrinkled, inelastic dehydrated and when it shows clear symptoms of premature ageing, it is most likely that its germinative layer is more or less seriously atrophied.

It is in fact known that the germinative layer of the skin consists of continuously reproducing and growing cells and that it requires a continuous feeding of nutrient substances to be maintained in a vital and efficient condition.

It is known as well that such a feeding takes place by blood circulation.

When blood circulation towards and within the germinative layer is hindered, or the feeding of nutrient substances is reduced, this layer becomes more and more atrophied and the skin becomes wrinkled and old-looking.

In the particular case of the hair, for the matrix and the papilla, which are involved by an intense metabolism, it is even more necessary to provide in a relevant amount the nutrient substances required for their trophism: as it is known, a lack of said substances would firstly cause the weakening and then the atrophy of the hair follicle, with attendant lack of capacity far forming new hair.

The cosmetic preparations for more or less specific topic treatment of the skin which have been up to date of wide use in order to attenuate the aforesaid conditions, are in most cases mere palliatives, the efficacy of which finds well known limits, essentially imputable to the fact that it is not possible through them to afford to the skin germinative layer the or those few nutrient substances which said preparations may comprise in their composition.

PRIOR DISCLOSURES

In the literature too, several proposals are described for the solution of the afore said problem.

a) In German published application No. 2,317,138 a preparation against hair fall is described, essentially consisting of a serum extracted from snakes, animals, particularly from snakes, serum which is used either as such or suitably concentrated and processed.

The above specification also contemplates the addition to the serum of simple molecules, aminoacids, vitamins, hormones, etc.

b) In French Patent No. 2,472,385 the use is taught, in the cosmetic field, of the product of thermal cracking of serums, tissue extracts and the like, the cracking being continued until peptides of a molecular weight of between 5000 and 50,000 are obtained. It is in fact known that peptides have the property of influencing cell growth.

c) In French patent No. 2,160,285 the use of lyophylized product is taught in the cosmetic field. This product is obtained from several serums, amniotic liquid or placenta.

d) The French patent No. 1,303,571 teaches the use, in the cosmetic field, of preparations containing one or more biocatalyst complexes, mainly of proteic nature, formed by combining biochemical or chemical compounds, having a certain nutrient action toward the skin, with biochemical products suitable for accelerating cutaneous cellular metabolism, such as hormones, vitamins, etc.

The common feature of all these products and preparations is their biological and extractive origin, whereby their production cannot be adequately standardized, with evident consequences, especially as regards the constancy of the effects. Moreover, it must be noted that not only the presence or absence, but also the amount of single components of the subject mixture seem to be important.

For the in vitro culture of epithelial cells the use is known of a synthetic nutrient medium comprising a mixture of simple and quantitatively defined molecules. It is also known that the synthetic medium, in order to obtain a more time extended action on the cultures, must be supplemented with a determined amount of a natural medium.

The problem not yet solved until now is that of providing a cosmetic preparation which does not only comprise all the nutrient substances which are essential in order to maintain in a vital and efficient condition the germinative layer of the skin and the piliferous papilla, but does also ensure a substantial amount, balanced and complete, of these substances thereto.

SUMMARY OF THE INVENTION

The aforesaid problem is solved according to the present invention by means of a cosmetic preparation for the topical treatment of the skin in order to promote its cellular trophism, comprising an effective amount of a nutrient medium for in vitro culture of isolated human epithelial cells, and an amount of bovine fetal serum related to the amount being used of said nutrient medium.

More particularly a cosmetic preparation according to the invention comprises, as a weight percentage referred to the total weight of the preparation, from 0.1 to 1% of said nutrient medium for the in vitro culture of isolated human epithelial cells and from 2 to 10% of serum of bovine fetus.

Considering the conventional mode of application of a cosmetic preparation and the well known impermeability of the skin towards almost all the aforesaid nutrient substances (since the factor limiting the cutaneous absorption is, as it is well known, the horny layer of the skin), said nutrient substances should be preferably present in their simplest form and have a low molecular weight: for instance aminoacids instead of proteins, nucleic bases instead of nucleic acids, pentoses and hexoses instead of polysaccharides, etc.

Moreover also to promote the permeation of said nutrient substances through the skin, the cosmetic preparation of the present invention comprises dermophilic vehicles, such as for instance ethyl alcohol, polyalcohols or glycols and generally emulsifiers, of the type conventionally used for such a purpose.

It is known that lotions for topical use based on extractive mixtures from the connective tissues of animals organs (such as for example Tricosaccaride, also written as "Trichosaccharide") mainly comprising sulfamuccopolysaccharides (or glycosaminoglycosanes), can be advantageously used in order to normalize the functions of the piliferous papillae and of the related germinative cells.

The action of these substances involves the small blood vessels which feed the pilosebaceous follicle, restoring the normal conditions of local circulation. The concentration range of the active substance in these solutions may vary from 0.2 to 3%.

It has now been surprisingly found that the combination of these substances with the previously considered active compounds and which are the subject of the present invention, forms a composition which does not only act simultaneously on both causes leading to hair fall (local circulatory lack and insufficient contribution of nutrient elements), but does also show an unexpected synergism with respect to that expected from the sum of the single components.

According to the invention it has been found that the extractive mixtures and the nutrient compositions for mediums of cellular cultures show, within some ratios, a relevant action synergism with an improvement of the efficacy of both active substances, the combination of which permits moreover, as above mentioned, to act on all the factors causing hair fall.

It is thus a further object of the present invention to provide a composition for the stimulation of trichogenesis comprising a first active component consisting of extractive mixtures obtained from connective tissues of animal organs and a second active component consisting of a nutrient medium for the in vitro culture of human epithelial cells.

It is known that a nutrient medium for the in vitro culture of isolated human cells contains all the nutrient elements necessary for the life of the cells and for their survival and reproduction.

The topical application of a cosmetic preparation according to the invention, which is an in vivo application generally carried out in the skin areas wherein the blood flow and thus the feeding of nutrient substances is most hindered and slowed, has proven to cause a substantial improvement of the local trophic conditions and a consequent normalization of the vitality and reproducing activity of the cells.

It has moreover been found that mineral salts, normally present in the medium for the in vitro culture of isolated human cells, preferably must be absent in the nutrient medium incorporated in the cosmetic preparation according to the present invention. As a matter of fact, whilst the mineral salts, in the strict sense, are not nutrient substances, they are already present in the cellular liquids.

Moreover, in order to take it into account the unavoidable dispersion of nutrient substances at the time of the application of a cosmetic preparation according to the invention, the concentration of the nutrient substances in the medium incorporated in said preparation must be 3 to 5 times greater than the concentration of said substances in the like medium used for the in vitro culture of isolated human epithelial cells.

Further features of the present invention shall appear more clearly from the following description in which is given a composition of a nutrient medium in a preparation according to the invention and wherein examples are given of cosmetic formulations based on the aforesaid product.

Example of composition of a powder nutrient medium to be incorporated in a cosmetic preparation according to the invention (percentage formula)

| | | | |
|---|---|---|---|
| L-Alanin | g 3.1997 | Choline hydrochloride | g 0.0639 |
| L-Arginine | g 8.9595 | Folic acid | g 0.0012 |
| L-Aspartic acid | g 3.8397 | i-Inositol | g 0.0063 |
| L-Cystine disodium salt | g 3.0282 | Menaphtone Na-bisulphite | g 0.0024 |
| L-Cysteine HCL | g 0.0126 | Nicotinic acid | g 0.0031 |
| L-Glutamic acid | g 8.5524 | Nicotinamide | g 0.0031 |
| L-Glutamine | g 12.7991 | p-Aminobenzoic acid | g 0.0063 |
| Glutathione | g 0.0063 | pyridoxal HCl | g 0.0031 |
| Glycine | g 6.4086 | Pyridoxine HCl | g 0.0031 |
| L-Histidine HCl.H$_2$O | g 2.8004 | Riboflavin | g 0.0012 |
| | | Thiamine HCl | g 0.0012 |
| L-hydroxyproline | g 1.2799 | DL-Tocopherol Na phosphate | g 0.0012 |
| L-Isoleucine | g 2.5598 | | |
| L-Leucine | g 7.6795 | Vitamin A acetate | g 0.0146 |
| L-Lysine HCl | g 8.9594 | Adenine sulfate | g 1,2799 |
| L-Methionine | g 1.9198 | 5-AMP | g 0.0256 |
| L-Phenylalanine | g 3.1997 | ATP disodium salt | g 1.2799 |
| L-Proline | g 5.1196 | S-Deoxiribose | g 0.0639 |
| L-Serine | g 3.1997 | Hypoxanthose | g 0.0384 |
| L-Triptophane | g 1.2799 | Ribose | g 0.0639 |
| L-Tyrosine | g 5.1196 | Thymine | g 0.0384 |
| L-Valine | g 3.1997 | Uracil | g 0.0384 |
| L-Ascorbic acid | g 0.0063 | Xanthene | g 0.0384 |
| Biotin | g 0.0012 | | |
| Calciteral | g 0.0127 | | |
| D-calcium Pantophenate | g 0.0012 | | |

This composition is prepared by operating in an environment having moisture less than 40%; all the components are weighed in order and the resulting mixture is charged in a ball mill wherein it is finely ground. The resulting powder is protected from moisture.

Examples of formulations for anti-wrinkle, hydrating and revitalizing products for the skin.

EXAMPLE 1

| Cream | |
|---|---|
| Medium of the invention | g 0.4 |
| fetal bovine serum | g 2.5 |
| polyglycol stearate | g 5.0 |
| stearine | g 6.5 |
| lanoline oil | g 6 |
| squalane | g 2 |
| spermaceti | g 8 |
| preservants and perfume | q.b. |
| H$_2$O the remaining to | g 100 |

EXAMPLE 2

| Milk | |
|---|---|
| Medium of invention | g 0.3 |
| fetal serum | g 2 |
| polyoxyethyleneglycol palmitostearate | g 5 |
| lanoline oil | g 5 |
| glyceryl monostearate | g 1 |
| propylene glycol | g 4 |
| preservants and perfumes | q.a. |
| H$_2$O the remaining to | g 100 |

EXAMPLE 3

| Lotion | |
|---|---|
| Concentrated medium | g 0.2 |

-continued

| Lotion | |
|---|---|
| fetal serum | g 2.5 |
| glucose | g 0.1 |
| alcohol 95° | ml 18 |
| Hamamelis extract | g 1 |
| ethoxylated lanoline | g 2 |
| glycerine | g 5 |
| preservants and perfumes | q.b. |
| H₂O the remaining to | ml 100 |

EXAMPLES OF LOTIONS FOR THE HAIR GROWTH

EXAMPLE 4

| | |
|---|---|
| Concentrated medium | g 0.5 |
| fetal serum | g 8 |
| glucose | g 0.1 |
| alcohol 95° | ml 3.5 |
| preservants and perfumes | q.b. |
| H₂O the remaining to | ml 100 |

EXAMPLE 5

| | |
|---|---|
| Concentrated medium | g 0.3 |
| fetal serum | g 5 |
| alcohol 95° | ml 20 |
| propylene glycol | g 3 |
| preservants and perfume | q.b. |
| H₂O the remaining to | ml 100 |

EXAMPLE 6

| | |
|---|---|
| Concentrated medium | g 0.2 |
| fetal serum | g 2 |
| Tween 80 | g 0.01 |
| nettle extract | g 3 |
| capsicum extract | g 1 |
| preservants and perfume | q.b. |
| H₂O the remaining to | ml 100 |

As previously mentioned, within the scope of the invention it has also been found that the above described nutrient compositions and the extracted mixtures from connective tissues of animal organs show, within some ranges, a relevant synergism of action, with the attendant improvement of the efficacy of both active substances. As already indicated, amongst the active agents for the stimulation of the local blood circulation, there are preferred for the present invention the extractive mixtures from connective tissues of animal organs, known as "Tricosaccaride", in the form of lotions.

Also known as "trichosaccharides", these are complex active principles extracted from the fundamental substance of the connective tissue of animal organs. Their aminomucopolysaccharide nature indicates that they have an important biological role and numerous practical applications. When tests were made to show that these substances were able to reduce the concentration of lipides in the blood, particularly in case of arteriosclerosis, it was noticed that they had a stimulating effect on hair growth in animals. Because of the complexity of their formula, analytical tests are systematiclly made on the tricosaccharides to ensure a standardized product with a constant content of hexuronic acids, hexosamines, amino acids and sulfur. Of course in the present invention use can be made of other already known active components, as vegetal extracts, such as nettle, Hamamelis, birch extracts or other components capable of stimulating the scalp as vasodilating agents, such as capsicine, esters of nicotinic acid (for instance, methyl and ethyl nicotinate). Hereinafter some examples of recipes of formulation of the active components of the preparation of the invention and of their mixtures are reported.

EXAMPLE 7

| Example of composition of the lotion based on the extractive mixture (composition A). | |
|---|---|
| 95% ethyl alcohol | ml 15 |
| propylene glycol | g 1.5 |
| preservant and perfume | g 0.8 |
| extractive mixture (Tricosaccaride) | g 1 |
| water remaining to | ml 100 |

EXAMPLE 8

| Examples of composition of medium and serum of bovine fetus and vehicle according to the invention (composition B) | |
|---|---|
| Medium + serum of bovine phoetus | g 62.5 |
| inositol | g 12.5 |
| mannitol | g 25 |

EXAMPLE 9

| Examples of lotions according to the present invention (composition C). | | | | |
|---|---|---|---|---|
| Component B (mg) | 100 | 400 | 700 | 1000 |
| Component A (g or ml) | 100 | 100 | 100 | 100 |
| Concentration of B | 0.1% | 0.4% | 0.7% | 1% |

The composition C of the invention was tested in comparison with the preparation used in the prior art, namely lotions based on extractive mixtures (composition A). For the experiments five tawny rabbits of Burgundy were used, the animals being normally fed, weighing 2.8 kg and being previously shaven on all the dorsal area. In order to more rapidly put into evidence the results of the experiments it was preferred to subcutaneously inject the preparations, instead of using the topical application which does not permit the stimulation of the new growth to be revealed in the animal.

The day after shawing, 0.1 ml of the following solutions, prepared at the moment, were injected:
1) extractive mixture (composition A) in 1% w/v aqueous solution;
2) 1% extractive mixture and 0.5% of composition B (weight by volume) in aqueous solution.

The two injections were carried out in the back, at two different heights and in a double test for each solution. The injections were repeated for two periods of five days in succession, with an interval of two rest days.

The tests gave the following results.

The solution (1) caused the fresh growth of the coat or hair around the injection area.

The fresh growth was clearly seen about 15 days from the begining of the injection. The solution (2) in turn caused a more rapid fresh growth, which moreover involved a more extended area than respect to that obtained, for each animal, with the sole solution (1).

As already mentioned, the present invention provides also an anti-wrinkle, hydrating and revitalizing action for the skin. In the following examples 10 to 13 the preparation of a cream, a milk and a lotion is illustrated.

EXAMPLE 10

A planetary mill of stainless steel is charged with 90% of the water necessary for the preparation of the cream and then the temperature is raised to 70° to 80° C. Parallely a separate melter is charged with polyglcol stearate, stearin, lanolin oil, squalane and preservants, bringing the temperature to a value of between 70° and 80° C. and starting the mixing action as soon as possible.

When the temperatures of the aqueous phase and of the fatty phase are in equilibrium, the fatty phase is poured into the water. The planetary mixing is started and the mixture is slowly cooled.

When the mass has reached 35° C., there are added the concentrated medium, previously dispersed in the 10% of water, the serum of bovine fetus and the perfume. Then the cooling is completed by keeping the mass under stirring.

EXAMPLE 11

A planetary mill of stainless steel is charged with 90% of the water needed for the preparation of milk and with the propylene glycol. The temperature is brought to between 70° C. and 80° C.

Parallelly, a separate mixer is charged with polyglycol stearate, lanoline oil, glyceryl monostearate and preservatives, bringing the temperature to between 70° C. and 80° C. and starting the mixing as soon as possible.

When the temperature of the aqueous phase and of the fatty phase are in equilibrium, the fatty phase is poured into the water. The planetary mixing is started and the mass is slowly cooled.

When the mass has reached 35° C., there are added the concentrated medium, as a predispersion in 10% of the water, fetal serum and the perfume. The cooling is then completed by keeping the mass stirred.

EXAMPLE 12

A vessel of stainless steel, fitted with a stirrer is charged in the order with 90% of the needed water, then with the concentrated medium, serum, glucose, Hamamelis extract, glycerine, preservatives and perfume.

The mixing is started and then ethoxylated lanoline is added, in a form predissolved in the remaining 10% of hot water. The mass is stirred for 15 minutes and then added with the alcohol and stirred again.

The pH is brought to 6.5 with diluted sodium hydroxide or HCl, then the mass is filtered in a filter of the type Seitz US and then bottled.

EXAMPLE 13

A stainless steel vessel, fitted with a stirrer, is charged with the necessary water and then with all the components according to example 7, whereas the solid mixture is separately prepared according to example 8. The mass is stirred for about 20 minutes, and then checked to verify whether the pH is 6.5; if necessary the pH is adjusted with diluted sodium hydroxide or HCl. After controlling the final volume the mass is stirred again for five minutes and the solution is maintained at rest for a night, and then filtered in a clarifying filter of the type Seitz US.

After filtration, packaging is carried out, comprising the bottling of the solution and the simultaneous dosing of the solid mixture in the reservoir-plug.

I claim:

1. Cosmetic preparation to promote the trophism of the skin and of the related piliferous follicles, consisting essentially of as a percent weight of said preparation, from 0.1 to 1% of said nutrient medium for in vitro culture of isolated human epithelial cells and from 2 to 10% of fetal bovine serum.

2. A process for the production of cosmetic preparations for topical treatment of the skin to promote the cellular trophism of the skin and of related piliferous follicles, comprising the steps of:

combining 0.2 to 0.5 g of a nutrient medium for in vitro culture of isolated human epithilial cells and 2 to 8 g of fetal bovine serum as a second active ingredient and related to the amount of said nutrient medium being used.

3. The process according to claim 2, wherein said nutrient medium has the following composition:

| | |
|---|---|
| L-Alanine | g 3.1997 |
| L-Arginine | g 8.9595 |
| L-Aspartic acid | g 3.8397 |
| L-Cystine disodium salt | g 3.0282 |
| L-Cysteine HCl | g 0.0126 |
| L-Glutamic acid | g 8.5524 |
| L-Glutamine | g 12.7991 |
| Glutathione | g 0.0063 |
| Glycine | g 4.4086 |
| L-Histidine HCl.H$_2$O | g 2.8004 |
| L-hydroxyproline | g 1.2799 |
| L-Isoleucine | g 2.5598 |
| L-Leucine | g 7.6795 |
| L-Lysine HCl | g 8.9594 |
| L-Methionine | g 1.9198 |
| L-Phenylalanine | g 3.1997 |
| L-Proline | g 5.1196 |
| L-Serine | g 3.1997 |
| L-Tryptophan | g 1.2799 |
| L-Tyrosine | g 5.1196 |
| L-Valine | g 3.1997 |
| L-Ascorbic Acid | g 0.0063 |
| Biotin | g 0.0012 |
| Calciferal | g 0.0127 |
| D-calcium pantothenate | g 0.0012 |
| Choline hydrochloride | g 0.0639 |
| Folic Acid | g 0.0012 |
| i-Inositol | g 0.0063 |
| Menaphtone Na-bisulte | g 0.0024 |
| Nicotinic acid | g 0.0031 |
| Nicotinamide | g 0.0031 |
| p-Aminobenzoic acid | g 0.0063 |
| Pyridoxal HCl | g 0.0031 |
| Pyridoxine Hcl | g 0.0031 |
| Riboflavin | g 0.0012 |
| Thiamine HCl | g 0.0012 |
| DL-Tocopherol Na phosphate | g 0.0012 |
| Vitamin A acetate | g 0.0146 |
| Adenine sulfate | g 1.2799 |
| 5-AMP | g 0.0256 |
| ATP disodium salt | g 1.2799 |
| S-Deoxyribose | g 0.0639 |
| Hypoxanthose | g 0.0384 |
| Ribose | g 0.0639 |
| Thiamine | g 0.0384 |
| Uracil | g 0.0384 |
| Xanthine | g 0.0384. |

4. The process according to claim 3, further comprising a dermophilic vehicle selected from the group consisting of ethyl alcohol, polyalcohols and glycols.

5. The process according to claim 3, further comprising emulsifiers.

6. The process according to claim 2, consisting essentially of as a percent weight of said preparation, from 0.1 to 1.0% of said nutrient medium and from 2 to 10% of said fetal bovine serum.

7. The process according to claim 2, wherein said nutrient medium is devoid of mineral salts.

8. The process according to claim 2, further comprising an additional active ingredient consisting of extractive mixtures obtained from connective tissues of animal organs.

9. The process according to claim 8, wherein the percent weight concentration of said additional active ingredient, per 100 parts by weight of composition, is between 0.1 and 10%.

10. The process according to claim 8, wherein said percent weight concentration of said additional active ingredient is between 0.3 and 0.6%.

11. The process according to claim 8, wherein said additional active ingredient is a tricosaccharide containing mainly polymucosaccharides of low molecular weight.

12. The process according to claim 2, wherein said cosmetic preparations are in the form of a cream, hydrating-revitalizing milk, or hair lotion.

13. The process according to claim 6, wherein said cosmetic preparations are in the form of a cream, hydrating-revitalizing milk, or hair lotion.

14. A process for the preparation of a cosmetic preparation for use as a cosmetic to promote the trophism of the skin and of related piliferous follicles, consisting essentially of providing, as a percent weight of said preparation, an amount of 0.1 to 1% of a nutrient medium for in vitro culture of isolated human epithelial cells and 2 to 10% of a fetal bovine serum which is related to the amount of said nutrient medium being used.

15. The process according to claim 14, additionally consisting of providing a dermophilic vehicle selected from the group consisting of ethyl alcohol, polyalcohols, glycols and emulsifiers.

16. A preparation for use as a cosmetic to promote the trophism of the skin and of the related piliferous follicles, consisting essentially of, as a percent weight of said preparation, 0.1 to 1% of a nutrient medium for in vitro culture of isolated human epithelial cells and 2 to 10% of fetal bovine serum which is related to the amount of said nutrient medium being used and an additional active ingredient consisting of extractive mixtures obtained from connective tissues of animal organs.

17. The preparation according to claim 16, wherein the percent weight concentration of said additional active ingredient, per 100 parts by weight of composition, is between 0.1 and 10%.

18. The preparation according to claim 17, wherein said weight concentration is solely between 0.3 to 0.6%.

19. Cosmetic preparation according to claim 16, wherein said additional ingredient is a trichosaccharide and consists mainly of sulfomuccopolysaccharides or glycoaminoglycosanes.

20. The preparation according to claim 16, wherein said nutrient medium has the following composition:

| | |
|---|---|
| L-Alanine | g 3.1997 |
| L-Arginine | g 8.9595 |
| L-Aspartic acid | g 3.8397 |
| L-Cystine disodium salt | g 3.0282 |
| L-Cysteine HCl | g 0.0126 |
| L-Glutamic acid | g 8.5524 |
| L-Glutamine | g 12.7991 |
| Glutathione | g 0.0063 |
| Glycine | g 4.4086 |
| L-Histidine HCl.H$_2$O | g 2.8004 |
| L-hydroxyproline | g 1.2799 |
| L-Isoleucine | g 2.5598 |
| L-Leucine | g 7.6795 |
| L-Lysine HCl | g 8.9594 |
| L-Methionine | g 1.9198 |
| L-Phenylalanine | g 3.1997 |
| L-Proline | g 5.1196 |
| L-Serine | g 3.1997 |
| L-Tryptophan | g 1.2799 |
| L-Tyrosine | g 5.1196 |
| L-Valine | g 3.1997 |
| L-Ascorbic Acid | g 0.0063 |
| Biotin | g 0.0012 |
| Calciferal | g 0.0127 |
| D-calcium pantothenate | g 0.0012 |
| Choline hydrochloride | g 0.0639 |
| Folic Acid | g 0.0012 |
| i-Inositol | g 0.0063 |
| Menaphtone Na-bisulte | g 0.0024 |
| Nicotinic acid | g 0.0031 |
| Nicotinamide | g 0.0031 |
| p-Aminobenzoic acid | g 0.0063 |
| Pyridoxal HCl | g 0.0031 |
| Pyridoxine Hcl | g 0.0031 |
| Riboflavin | g 0.0012 |
| Thiamine HCl | g 0.0012 |
| DL-Tocopherol Na phosphate | g 0.0012 |
| Vitamin A acetate | g 0.0146 |
| Adenine sulfate | g 1.2799 |
| 5-AMP | g 0.0256 |
| ATP disodium salt | g 1.2799 |
| S-Deoxyribose | g 0.0639 |
| Hypoxanthose | g 0.0384 |
| Ribose | g 0.0639 |
| Thiamine | g 0.0384 |
| Uracil | g 0.0384 |
| Xanthine | g 0.0384. |

* * * * *